(12) United States Patent
Herrmann

(10) Patent No.: US 7,045,142 B2
(45) Date of Patent: *May 16, 2006

(54) SUSTAINED RELEASE OF SUPEROXIDE DISMUTASE MIMICS FROM IMPLANTABLE OF INSERTABLE MEDICAL DEVICES

(75) Inventor: Robert A. Herrmann, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/951,264

(22) Filed: Sep. 27, 2004

(65) Prior Publication Data

US 2005/0112174 A1    May 26, 2005

Related U.S. Application Data

(63) Continuation of application No. 10/170,268, filed on Jun. 11, 2002, now Pat. No. 6,835,387.

(51) Int. Cl.
*A61M 25/00* (2006.01)
*A61M 29/00* (2006.01)

(52) U.S. Cl. .................. 424/425; 424/400; 424/422; 424/423; 424/424

(58) Field of Classification Search ............. 424/400, 424/422, 423, 424, 425
See application file for complete search history.

(56) References Cited

U.S. PATENT DOCUMENTS

| | | | |
|---|---|---|---|
| 5,403,834 | A | 4/1995 | Malfroy-Camine et al. |
| 5,696,109 | A | 12/1997 | Malfroy-Camine et al. |
| 5,873,904 | A | 2/1999 | Ragheb et al. |
| 5,874,421 | A | 2/1999 | Riley et al. |
| 6,057,367 | A | 5/2000 | Stamler et al. |
| 6,084,093 | A | 7/2000 | Riley et al. |
| 6,096,070 | A | 8/2000 | Ragheb et al. |
| 6,103,714 | A | 8/2000 | Fridovich et al. |
| 6,214,817 | B1 | 4/2001 | Riley et al. |
| 6,218,016 | B1 | 4/2001 | Tedeschi et al. |
| 6,290,949 | B1 | 9/2001 | French et al. |
| 6,306,421 | B1 | 10/2001 | Kunz et al. ............... 424/423 |
| 6,541,116 | B1 * | 4/2003 | Michal et al. ............ 428/420 |
| 6,545,097 | B1 * | 4/2003 | Pinchuk et al. ........... 525/240 |
| 6,605,619 | B1 * | 8/2003 | Mitchell et al. .......... 514/315 |
| 2001/0018072 | A1 | 8/2001 | Unger ...................... 424/484 |
| 2002/0009535 | A1 | 1/2002 | Michal et al. ............. 427/2.1 |
| 2002/0128248 | A1 * | 9/2002 | Salvemini ................. 514/185 |

FOREIGN PATENT DOCUMENTS

| | | |
|---|---|---|
| WO | WO 98/36784 | 8/1998 |
| WO | WO 00/72893 A2 | 12/2000 |
| WO | WO 01/54748 A1 | 8/2001 |

OTHER PUBLICATIONS

Kishore Udipi et al., "Modification of Inflammatory Response to Implanted Biomedical Materials in vivo by Surface Bound Superoxide Dismutase Mimics," *Journal of Biomedical Materials Research*, vol. 15, No. 4, 2000, pp. 549-560.

Q.J. Xie et al., Study on plated-derived growth factor mRNA and copper-zinc superoxide dismutase mRNA expression changes of aortic artery endothelium with restenosis after aortic artery dilatation treated with buyang huanwu decoction, *Zhongguo Zhong Xi Yi Jie He Za Zhi*, vol. 17, No. 10, Oct. 1997, pp. 611-613. Abstract only.

Jun Luo, "Nitroxides—Metal-Dependent SOD Mimics," B-180 Medical Laboratories, Free Radical and Radiation Biology Program, University of Iowa, vol. 77, No. 222, Spring 2001, pp. 1-10.

T. Oinuma et al., "Effects of Copper-Zinc Type Superoxide Dismutase on the Proliferation and Migration of Cultured Vascular Smooth Muscle Cells Induced by Oxidized Low Density Lipoprotein," *J. Atheroscler. Thromb.*, vol. 4, No. 2, 1997, pp. 79-84. Abstract only.

P.F. Li et al., "Differential Effect of Hydrogen Peroxide and Superoxide Anion on Apoptosis and Proliferation of Vascular Smooth Muscle Cells," *Circulation*, vol. 96, No. 10, Nov. 18, 1997, pp. 3602-3609. Abstract only.

(Continued)

*Primary Examiner*—Michael Hartley
*Assistant Examiner*—Simon J. Oh
(74) *Attorney, Agent, or Firm*—Mayer & Williams PC; David B. Bonham, Esq.

(57) ABSTRACT

An implantable or insertable medical device is provided which comprises (a) a superoxide dismutase mimic and (b) a polymeric release region. Upon administration to a patient, the polymeric release region controls the release of the superoxide dismutase mimic, which is beneficially selected from a metal-chelate superoxide dismutase mimic and a nitroxide superoxide dismutase mimic. Also provided is a method of making an implantable or insertable medical device.

18 Claims, No Drawings

OTHER PUBLICATIONS

X.C. Zheng et al., Expression of human superoxide dismutase gene in rat vascular smooth muscle cells and its anti-oxidative effect, *Sheng Li Xue Bao*, vol. 15, No. 2, Apr. 1999, pp. 199-205. Abstract only.

L.C. Azevedo et al., "Oxidative Stress as a Signaling Mechanism of the Vascular Response to Injury: The Redox Hypothesis of Restenosis," *Cardiovas. Res.*, vol. 47, No. 3, Aug. 18, 2000, pp. 436-445. Abstract only.

Min Wang, "SOD Mimics," B180 Med Lab, University of Iowa, vol. 77, No. 222, Spring 2001, pp. 1-10.

Tal Offer et al., "The Pro-Oxidative Activity of SOD and Nitroxide SOD Mimics," *The FASEB Journal*, vol. 14, Jun. 2000, pp. 1215-1223.

S Cuzzocrea et al., "Antioxidant Therapy: A New Pharmacological Approach in Shock, Inflammation, and Ischemia/Reperfusion Injury," *Pharmacol. Rev.*, vol. 53, No. 1, Mar. 2001, pp. 135-159.

N. Ahmad et al., "Metal-Independent Putative Superoxide Dismutase Mimics in Chemistry, Biology, and Medicine," *Ecotoxicol. Environ. Saf.*, vol. 34, No. 2, Jul. 1996, pp. 141-144. Abstract only.

T.P. Kasten et al., "Potentiation of Nitric Oxide-Mediated Vascular Relaxation by SC52608, a Superoxide Dismutase Mimic," *Proc. Soc. Exp. Biol. Med.*, vol. 208, No. 2, Feb. 1995, pp. 170-177. Abstract only.

* cited by examiner

SUSTAINED RELEASE OF SUPEROXIDE DISMUTASE MIMICS FROM IMPLANTABLE OF INSERTABLE MEDICAL DEVICES

STATEMENT OF RELATED APPLICATIONS

This application is a continuation of U.S. patent application Ser. No. 10/170,268 filed Jun. 11, 2002, now U.S. Pat. No. 6,835,387 entitled "Sustained Release Of Superoxide Dismutase Mimics From Implantable Or Insertable Medical Devices," which is incorporated by reference herein in its entirety.

BACKGROUND OF THE INVENTION

1. Field of the Invention

The present invention relates to implantable or insertable medical devices and more particularly to implantable or insertable medical devices comprising a polymer that releases a therapeutic agent.

2. Brief Description of the Background Art

Superoxide dismutase mimics are enzymes that catalyze dismutation of superoxide radicals ($O_2^-$) by converting them to less reactive hydrogen peroxide ($H_2O_2$) and dioxygen ($O_2$). The body's response to implanted biomedical materials typically involves inflammation to varying degrees. To address this inflammation, superoxide dismutase mimics have been covalently attached to the surfaces of various biomaterials for implantation. See Udipi, K. et al, "Modification of inflammatory response to implanted biomedical materials in vivo by surface bound superoxide dismutase mimics," *J. Biomed Mater. Res.* 2000 Sep. 15; 51(4):549–60.

Local delivery of therapeutic agents from implantable or insertable medical devices is an important new technology in the treatment of diseases.

For example, intraluminal stents are commonly inserted into the coronary artery after percutaneous transluminal coronary angioplasty procedures. Such stents are provided to maintain the patency of the coronary artery by supporting the arterial walls and preventing abrupt reclosure or collapse thereof, which can occur after the angioplasty procedure. However, the presence of a stent can exacerbate restenosis of the vessel.

In response to this problem, local delivery of a number of restenosis-inhibiting therapeutic agents (such as paclitaxel, rapamycin, nitric oxide donors, and so forth) from coatings of stents that have been inserted after percutaneous transluminal coronary angioplasty procedures has been proposed.

However, the technology associated with drug delivery from coated vascular medical devices such as coronary stents is a relatively new one. Moreover, while numerous therapeutic agents have been proposed as noted above, it is possible that certain of these agents will ultimately be found to act on an inappropriate cell physiology, or that they are not be presented to the vasculature in appropriate concentrations.

SUMMARY OF THE INVENTION

In accordance with the present invention, an implantable or insertable medical device, for example, a vascular stent, is provided which comprises (a) a superoxide dismutase mimic and (b) a polymeric release region. Upon administration to a patient, the polymeric release region controls the release of the superoxide dismutase mimic, which is beneficially selected from a metal-chelate superoxide dismutase mimic and a nitroxide superoxide dismutase mimic.

Examples of implantable or insertable medical devices appropriate for the practice of the present invention, besides vascular stents, include catheters, balloons, cerebral aneurysm filler coils and arterio-venous shunts as well as non-vascular stents such as biliary stents and renal stents.

In some embodiments, the superoxide dismutase mimic is a nitroxide compound, for example, 2,2,6,6-tetramethylpiperidine-1-yloxy, 4-hydroxytetramethyl-piperidine-1-oxyl or 4-hydroxy-2,2,6,6,-tetramethylpiperidine-1-N-oxyl. In other embodiments, the superoxide dismutase mimic is a metal-chelate compound, for example, a metal-pentaazacyclopentadecane compound, a metal-porphyrin compound, a metal-porphine compound, a metal-desferioxamine compound, a metal-bis(cyclohexylpyridine) compound or a salen-metal compound.

Typically, the polymeric release region is either a polymeric matrix within which the superoxide dismutase mimic is disposed, or a polymeric barrier layer that is disposed over the superoxide dismutase mimic. Numerous polymers can be used in the construction of the polymeric release region. One particularly preferred group of polymers are copolymers of isobutylene and styrene.

The medical devices of the present invention can be administered in the treatment of a number of diseases and conditions, including restenosis, gastrointestinal inflammation, and inflammatory processes involving the vasculature or other lumens within the body (e.g., duct inflammation).

The release profile associated with the devices of the present invention can be tailored to the treatment of interest. In some embodiments, the release profile is an extended release profile in which less than 50% of the total amount of superoxide dismutase mimic that is released into the vasculature from the medical device is released within the first 24 hours of administration.

According to further embodiments of the present invention, a method of forming an implantable or insertable medical device is provided. The method comprises: (a) providing a solution or dispersion comprising (i) a superoxide dismutase mimic selected from a metal-chelate superoxide dismutase mimic and a nitroxide superoxide dismutase mimic, (ii) a polymer and (iii) a solvent; (b) contacting the solution or dispersion with a medical device; and (c) removing the solvent to form a superoxide dismutase mimic-containing polymer matrix on the medical device. The solution or dispersion can be contacted with the medical device in a number of ways, including spraying the medical device with the solution or dispersion, or dipping the medical device in the solution or dispersion.

One advantage of the present invention is that implantable or insertable medical devices are provided, which enable the extended release of superoxide dismutase mimics from the device surface.

In contrast to prior art implantable biomedical materials in which superoxide dismutase mimics are covalently attached at the surface, the medical devices of the present invention are also advantageous at least in that: (1) the superoxide dismutase mimics are released to surrounding tissue, allowing the surrounding material to be treated, and (2) the amount of superoxide dismutase mimic provided can be an order of magnitude greater than that provided by surface attachment techniques.

A further advantage of the present invention is that treatment methods, including a method for the treatment of restenosis, are provided, which utilize the above medical devices.

In connection with the controlled release aspects of the devices of the present invention, yet another advantage is that a subject can be treated without significant risk of local overdose.

Still another advantage of the present invention is that, due to the catalytic nature of superoxide dismutase mimics, side effects are expected to be minimal.

These and other embodiments and advantages of the present invention will readily become apparent to those of ordinary skill in the art upon review of the Detailed Description and claims to follow.

DETAILED DESCRIPTION OF THE INVENTION

In accordance with various embodiments of the invention, implantable or insertable medical devices are provided that comprise a polymer release region for a superoxide dismutase mimic. Typically, the superoxide dismutase mimic is (a) disposed within the polymer release region, in which case the polymer release region may be referred to herein as a polymer matrix, or (b) disposed beneath the polymer release region, in which case the polymer release region may be referred to herein as a polymer barrier layer. As a result of the polymer release region, at least a portion of the superoxide dismutase mimic within the medical device is released upon administering the medical device to the vasculature a patient.

Diseases and conditions that are treated using the medical devices of the present invention include restenosis, gastrointestinal inflammation, and inflammatory processes involving the vasculature or other lumens within the body (e.g., duct inflammation). As used herein, "treatment" refers the prevention of a disease or condition, the reduction or elimination of symptoms associated with a disease or condition, or the substantial or complete elimination a disease or condition. Preferred subjects are vertebrate subjects, more preferably mammalian subjects and most preferably human subjects.

Superoxide dismutase mimics are enzymes that are understood to catalyze dismutation of superoxide radicals ($O_2^-$) by converting them to hydrogen peroxide ($H_2O_2$) and dioxygen ($O_2$). As a result, superoxide dismutase mimics are used in connection with the present invention to address the presence of overabundant superoxide associated with various diseases and conditions.

As one example, and without wishing to be bound by theory, superoxide dismutase mimics can be used to address the presence of overabundant superoxide in atherosclerotic lesions following stent implantation. By addressing this basic issue, it is believed that the inflammatory response to the stent is suppressed and restenosis is limited. Using the medical devices of the invention, the release of the superoxide dismutase mimic can be controlled and can provide a protective effect over an extended period of time. According to one specific embodiment of the invention, a coronary stent, which has an overall coating weight of about 500 µg (of which about 150 µg is superoxide dismutase mimic) and which releases the superoxide dismutase mimic over a period of 2–4 weeks, is implanted in the coronary artery to combat restenosis.

Superoxide dismutase mimics are preferred over the endogenous superoxide dismutase enzyme for the practice of the invention for a number of reasons, including the fact that they are typically smaller than the endogenous superoxide dismutase enzyme and hence are better able to diffuse from the medical device and into the tissue surrounding the medical device (e.g., the media and adventitia of a coronary artery adjacent a stent).

Superoxide dismutase mimics can be broken down into two groups: metal-dependent superoxide dismutase mimics and metal-independent superoxide dismutase mimics. The metal dependent superoxide dismutase mimics typically comprise a transition metal such as Mn, Cu or Fe. The metal-independent superoxide dismutase mimics typically are nitroxide complexes.

Preferred metal-dependent superoxide dismutase mimics are metal-chelate compounds and include (a) metal-pentaazacyclopentadecane superoxide dismutase mimics, including Mn[II] dichloro(1,4,7,10,13-pentaazacyclopentadecane) (MnPAM), Mn[II] dichloro(2R,3R,8R,9R-bis-cyclohexano-1,4,7,10,13-pentaazacyclopentadecane) (SC-55858), as well as other pentaazacyclopentadecanes such as those described in U.S. Pat. Nos. 6,214,817 and 5,874,421, which are hereby incorporated by reference; (b) metal-porphyrin superoxide dismutase mimics including Mn[III] tetrakis(4-benzoic acid)porphyrin (MnTBAP), Mn[III] tetrakis(1-methyl-4-pyridyl) porphyrin, (MnTMPyP), Mn[III] tetra(4-pyridyl)porphyrin, (MnTPyP), Mn[III] tetrakis(trimethylammonio)phenyl porphyrin (MnTMAP), as well as other metal-porphyrin superoxide dismutase mimics such as those disclosed in U.S. Pat. No. 6,103,714, which is hereby incorporated by reference; (c) metal-porphine superoxide dismutase mimics including Fe[III] tetrakis(4-N-methylpyridyl)porphine (FeTMPP); (d) metal-desferioxamine superoxide dismutase mimics including manganese desferioxamine (Mndf); (e) Fe[II]tetrakis-N,N,N',N'-(2-pyridylmethyl)ethylenediamine (Fe(II)TPEN); (f) metal-bis(cyclohexylpyridine) compounds, including M40403, a manganese(II) complex with a bis(cyclohexylpyridine)-substituted ligand; (g) Cu(II)-tetraanhydro-aminobenzaldehyde (TAAB); and (h) salen-metal superoxide dismutase mimics, including salen-Mn, salen-Co, salen-Fe, salen-V, salen-Cr and salen-Ni complexes, such those described in U.S. Pat. No. 5,696,109, which is hereby incorporated by reference.

Metal-independent superoxide dismutase mimics include nitroxide superoxide dismutase mimics such as 2,2,6,6-tetramethylpiperidine-1-yloxy (TEMPO), 4-hydroxytetramethyl-piperidine-1-oxyl (TEMPOL) and 4-hydroxy-2,2,6,6,-tetramethylpiperidine-1-N-oxyl (TPL).

Metal-chelate superoxide dismutase mimics such as those discussed above are particularly preferred for the practice of the present invention.

Preferred implantable or insertable medical devices for use in conjunction with the present invention include vascular and non-vascular medical devices, including catheters, guide wires, balloons, filters (e.g., vena cava filters), stents (e.g., coronary vascular stents, cerebral stents, renal stents including urethral stents and ureteral stents, biliary stents, tracheal stents, gastrointestinal stents and esophageal stents), arterio-venous shunts, stent grafts, cerebral aneurysm filler coils (including GDC [Guglilmi detachable coils] and metal coils), vascular grafts, myocardial plugs, patches, pacemakers and pacemaker leads and heart valves.

Medical devices made in accordance with the present invention can be placed in a variety of bodily locations for contact with bodily tissue and/or fluid. Non-limiting examples are tumors; organs including but not limited to the heart, various body lumens, coronary or peripheral vascular system, lungs, trachea, esophagus, brain, liver, kidney, bladder, urethra and ureters, eye, intestines, stomach, pancreas, ovary, and prostate; skeletal muscle; smooth muscle; breast; cartilage; and bone.

Depending upon the application at hand, the polymer release region can be associated with the medical device in a number of ways. For example, the polymer release region can constitute the entirety of the medical device, or it can constitute just a portion of the medical device. The portion of the medical devices can be, for example, (a) one or more medical device coatings, (b) one or more entire medical device components, (c) one or more portions of medical device components, and so forth.

In many preferred embodiments, a polymer release region is provided in the form of a layer, for example, a coating on a medical device surface, including internal and/or external surfaces. The medical device surface or surfaces upon which the polymer release region is disposed can constitute a wide variety of materials, including glasses, metals, polymers, ceramics and combinations thereof.

Polymer materials for use in forming the polymer release region include essentially any polymeric material (including copolymers and polymer blends) that is compatible with the superoxide dismutase mimic, is compatible with the medical device, allows for the release of the superoxide dismutase mimic, is compatible with the administration site, and so forth. The polymers may be crosslinked or uncrosslinked, linear or branched, natural or synthetic, thermoplastic or thermosetting.

Exemplary polymers include the following: polycarboxylic acid polymers and copolymers including polyacrylic acids (e.g., acrylic latex dispersions and various polyacrylic acid products such as HYDROPLUS, available from Boston Scientific Corporation, Natick Mass. and described in U.S. Pat. No. 5,091,205, the disclosure of which is hereby incorporated herein by reference, and HYDROPASS, also available from Boston Scientific Corporation); acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polybismaleinimides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); anhydride polymers and copolymers including maleic anhydride polymers; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates (e.g., U.S. Pat. No. 5,091,205 describes medical devices coated with one or more polyisocyanates such that the devices become instantly lubricious when exposed to body fluids); polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes (e.g., BAYHYDROL polyurethane dispersions); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Block copolymers having at least two polymeric blocks A and B are one preferred group of polymers for use in connection with the present invention. Examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed molecule.

One specific preferred group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block with the triblock therefore denoted as BAB). Where n=3 or more, these structures are commonly referred to as star-shaped block copolymers.

The A blocks are preferably soft elastomeric components which are based upon one or more polyolefins, more preferably a polyolefinic block having alternating quaternary and secondary carbons of the general formulation: —(CRR'—CH$_2$)$_n$—, where R and R' are linear or branched aliphatic groups such as methyl, ethyl, propyl, isopropyl, butyl, isobutyl and so forth, or cyclic aliphatic groups such as cyclohexane, cyclopentane, and the like, with and without pendant groups. Polymers of isobutylene,

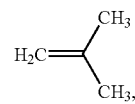

(i.e., polymers where R and R' are the same and are methyl groups) are more preferred.

The B blocks are preferably hard thermoplastic blocks that they, when combined with the soft A blocks, are capable of, inter alia, altering or adjusting the hardness of the resulting copolymer to achieve a desired combination of qualities. Preferred B blocks are polymers of methacrylates or polymers of vinyl aromatics. More preferred B blocks are (a) made from monomers of styrene

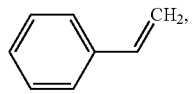

styrene derivatives (e.g., α-methylstyrene, ring-alkylated styrenes or ring-halogenated styrenes) or mixtures of the same or are (b) made from monomers of methylmethacrylate, ethylmethacrylate hydroxyethyl methacrylate or mixtures of the same.

Particularly preferred polymers for use in connection with the present invention include copolymers of polyisobutylene with polystyrene or polymethylstyrene, more preferably polystyrene-polyisobutylene-polystyrene triblock copolymers. These polymers are described, for example, in U.S. Pat. No. 5,741,331, U.S. Pat. No. 4,946,899 and U.S. Ser. No. 09/734,639, each of which is hereby incorporated by reference in its entirety.

The polymers above can also be used in connection with further auxiliary materials to achieve a desired result. Such auxiliary materials include binders, blending agents, and so forth.

Numerous techniques are available for creating polymer release regions in the form of medical devices or portions of medical devices, including polymer matrices and polymer barrier layers.

For example, where the selected polymer has thermoplastic characteristics, a variety of standard thermoplastic processing techniques can be used to form the polymer release region, including compression molding, injection molding, blow molding, spinning, vacuum forming and calendaring, as well as extrusion into sheets, fibers, rods, tubes and other cross-sectional profiles of various lengths. Using these and other techniques, devices such as balloons, catheters, stents and portions thereof can be made from.

As a specific example, where a polymer coating is desired, the coating can be, for example, co-extruded along with an underlying medical device or portion thereof.

If the superoxide dismutase mimic is stable at processing temperatures, then it can be combined with the polymer, for example, by extrusion, prior to thermoplastic processing, producing a superoxide dismutase mimic containing polymer matrix.

Polymer release regions can also be made using solvent-based techniques in which polymer is first dissolved in a solvent and the polymer solution is subsequently used to form the polymer release region. The solvent should, of course, be compatible with the polymer. Preferred solvent-based techniques of this nature include, but are not limited to, solvent casting, spin coating, web coating, solvent spraying, dipping, coating via air suspension and mechanical suspension techniques, positive displacement coating techniques, ink jet techniques, electrostatic techniques, and combinations of these processes.

If desired, the polymer/solvent mixture can contain more than one solvent (for example, one solvent appropriate for the polymer and a different solvent appropriate for the superoxide dismutase mimic).

In some solvent-based techniques, a solution comprising solvent and polymer is applied to a substrate. The substrate can be, for example, all or a portion of a medical device to which the polymer release region is applied as a coating.

The substrate can also be, for example, a template from which the polymer release region is removed after solvent elimination. Such template-based techniques are particularly appropriate for forming simple objects such as sheets, tubes, cylinders and so forth, which can be easily removed from a template substrate.

In other techniques, for example, fiber forming techniques, the polymer release region is formed without the aid of a substrate.

Where appropriate, techniques such as those listed above can be repeated or combined to build up a polymer release region to a desired thickness. Polymer release region thickness can be varied in other ways as well. For example, in solvent spraying, coating thickness can be increased by modification of coating process parameters, including increasing flow rate, slowing the movement between the device or template to be coated and the spray nozzle, providing repeated passes and so forth.

When forming polymer matrices using solvent-based techniques, and where the solvent is compatible with the superoxide dismutase mimic, the superoxide dismutase mimic can be provided in the polymer/solvent mixture, for example, in dissolved form or as a particulate suspension. Such techniques allow the superoxide dismutase mimic to be provided concurrently with component formation. Otherwise, the superoxide dismutase mimic can be added subsequent to polymer matrix formation as discussed below.

After forming the polymeric release region using solvent-based techniques, it is preferably dried to remove the solvents. In the case of a coating, the coating typically conforms to the underlying surface during the drying process.

In some embodiments, the superoxide dismutase mimic is provided within the polymer matrix subsequent to its formation. For example, the superoxide dismutase mimic can be dissolved in a solvent that is compatible with both the polymer and the superoxide dismutase mimic. Preferably, the polymer matrix is at most only slightly soluble in the solvent. Subsequently, the solution is contacted with the polymer matrix such that the superoxide dismutase mimic is provided within the polymer matrix (e.g., by leaching/diffusion into the polymer). For this purpose, the polymer matrix can be immersed or dipped into the solution, for example. Alternatively, the solution can be applied to polymer matrix, for example, by spraying. The polymer matrix can subsequently be dried, with the superoxide dismutase mimic remaining therein.

Regardless of the fashion by which the superoxide dismutase mimic is incorporated into the polymer matrix, a wide variety of superoxide dismutase mimic loadings are possible, with the amount of loading being readily determined by those of ordinary skill in the art, depending upon the release profile that is desired. The superoxide dismutase mimic containing polymeric matrix can will frequently comprise from 1% or less to 70 wt % or more superoxide dismutase mimic, with ranges of 1–2 wt %, 2–4 wt %, 4–8 wt %, 16–32 wt %, 32–68 wt %, among others being possible.

In some embodiments, the polymer release region is a polymer barrier layer. In these embodiments, the superoxide dismutase mimic is provided in a superoxide dismutase mimic containing layer below the polymer barrier layer and diffuses through the barrier to effect release. For example, the superoxide dismutase mimic-containing layer can be a precipitated layer of the superoxide dismutase mimic compound, or it can be provided in a polymeric layer, beneath the polymer barrier layer.

In accordance with the present invention, superoxide dismutase mimic is released via the polymer release region to a bodily tissue or bodily fluid upon contacting the same. The desired release profile is readily determined by those of ordinary skill in the art and ultimately depends upon the condition to be treated, the nature of the superoxide dismutase mimic itself, and so forth.

An extended release profile is preferred in many instances. By "extended release profile" is meant a release profile in which less than 50% of the total release from the medical device that occurs over the course of implantation/insertion in the body occurs within the first 24 hours of administration. Conversely, this means that more than 50% of the total release from the medical device will occur after the device has been implanted/inserted for 24 hours. Various extended release profiles can be provided in accordance with the present invention including: (a) the 50% release point occurring at a time that is between 24 and 48 hours after implantation/insertion, (b) the 50% release point occurring at a time that is between 48 and 96 hours after implantation/insertion, (c) the 50% release point occurring at a time that is between 96 and 168 hours (1 week) after implantation/insertion, (d) the 50% release point occurring at a time that is between 1 and 2 weeks after implantation/insertion, (e) the 50% release point occurring at a time that is between 2 and 4 weeks after implantation/insertion, (f) the 50% release point occurring at a time that is between 4 and 8 weeks after implantation/insertion, (g) the 50% release point occurring at a time that is between 8 and 16 weeks after implantation/insertion, and (h) the 50% release point occurring at a time that is between 16 and 32 weeks after implantation/insertion.

The release rate of superoxide dismutase mimic can be varied in a number of ways. Examples include: (a) varying the type of polymer within the release region, (b) varying the molecular weight of the polymers within the release region, (c) where a copolymer or polymer blend is used within the release region, varying the specific constituents of the copolymer or polymer blend, as well as the relative amounts of these constituents, (d) where solvent-based techniques are used to form the release region, varying the type and relative amounts of solvents used in processing the polymer release region, (e) varying the porosity of the polymers within the release region, and (f) providing an additional polymer layer over the release region to further retard diffusion.

The invention is further described with reference to the following non-limiting Example.

EXAMPLE

Stainless steel coronary stents are coated with a polymeric matrix containing a superoxide dismutase mimic of choice. The polymer matrix is a polystyrene-polyisobutylene-polystyrene triblock copolymer matrix, described, for example, in U.S. Pat. No. 5,741,331, U.S. Pat. No. 4,946,899 and U.S. Ser. No. 09/734,639, the disclosures of which are hereby incorporated by reference. The superoxide dismutase mimic is uniformly dispersed throughout the polymer. The coating is applied from a solution containing 1 wt % solids (SOD mimic and polymer), 74.3 wt % methylene chloride and 24.7 wt % toluene, by spray coating (or dip coating). The coating contains from 5–30% superoxide dismutase mimic by weight. Following coating of the device, the devices are dried in a vacuum oven at 40° C. for 1 hr. Extended release can be demonstrated by incubation of each coated stent in phosphate buffered saline (PBS) at 37° C. An extended release profile is desirable for coronary stents, because the restenotic process occurs over several weeks following stent implantation.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising:
   a superoxide dismutase mimic selected from a metal-chelate superoxide dismutase mimic and a nitroxide superoxide dismutase mimic; and
   a polymeric release region tat controls the release of said superoxide dismutase mimic upon administration to a patient;
   wherein the superoxide dismutase mimic is disposed within a polymeric matrix comprising a copolymer comprising an isobutylene monomer and a styrene monomer;
   and wherein the medical device is selected from a stent, a catheter, a balloon, a cerebral aneurysm filter coil, an arterio-venous shunt, a guide wire, a vena cava filter, a stent graft, a vascular graft, a myocardial plug, a patch, a pacemaker, a pacemaker lead, and a heart valve.

2. The implantable or insertable medical device of claim 1, wherein said stent is a vascular stent.

3. The implantable or insertable medical device of claim 1, wherein said medical device is a vascular medical device.

4. The implantable or insertable medical device of claim 1, wherein said superoxide dismutase mimic is a nitroxide compound.

5. The implantable or insertable medical device of claim 1, wherein said superoxide dismutase mimic is a nitroxide compound selected from 2,2,6,6-tetramethylpiperidine-1-yloxy, 4-hydroxytetramethyl-piperidine-1-oxyl and 4-hydroxy-2,2,6,6,-tetramethylpiperidine-1-N-oxyl.

6. The implantable or insertable medical device of claim 1, wherein said superoxide dismutase mimic is a metal-chelate compound.

7. The implantable or insertable medical device of claim 1, wherein said superoxide dismutase mimic is a metal-chelate compound selected from metal-pentaazacyclopentadecane compounds, metal-porphine compounds, metal-porphine compounds, metal-desferioxamine compounds, metal-bis(cyclohexylpyridine) compounds and salen-metal compounds.

8. A method for treating a disease or condition of the vasculature comprising implanting or inserting the medical device of claim 1 into the body of a patient.

9. A method for treating a disease or condition of the vasculature comprising implanting or inserting the medical device of claim 1 into the vasculature of a patient.

10. The method of claim 8, wherein 50% of the total amount of superoxide dismutase mimic that is released into the body from said medical device is released beyond 24 hours after administration.

11. The method of claim 9, wherein said disease or condition is restenosis.

12. A method of forming the implantable or insertable medical device of claim 1 comprising:

comprising said superoxide dismutase mimic, said copolymer and a solvent;

contacting said solution or dispersion with a medical device; and removing said solvent to form a superoxide dismutase mimic-containing polymeric matrix on said medical device, wherein said polymeric matrix controls the release of said superoxide dismutase mimic upon administration to a patient.

13. The method of claim 12, wherein said superoxide dismutase mimic is a nitroxide compound.

14. The method of claim 12, wherein said superoxide dismutase mimic is a nitroxide compound selected from 2,2,6,6-tetramethylpiperidine-1-yloxy, 4-hydroxytetramethyl-piperidine-1-oxyl and 4-hydroxy-2,2,6,6,-tetramethylpiperidine-1-N-oxyl.

15. The method of claim 12, wherein said superoxide dismutase mimic is a metal-chelate compound.

16. The method of claim 12, wherein said superoxide dismutase mimic is selected from metal-pentaazacyclopentadecane compounds, metal-porphine compounds, metal-porphine compounds, metal-desferioxamine compounds, metal-bis(cyclohexylpyridine) compounds and salen-metal compounds.

17. The method of claim 12, wherein said solution or dispersion is contacted with said medical device by spraying said medical device with said solution or dispersion.

18. The method of claim 12, wherein said solution or dispersion is contacted with said medical device by dipping said medical device in said solution or dispersion.

* * * * *